United States Patent
Holmqvist (10) Patent No.: US 11,865,297 B2
(45) Date of Patent: Jan. 9, 2024

(54) TRANSPORT LOCK ASSEMBLY, AND A MEDICAMENT DELIVERY DEVICE COMPRISING THE TRANSPORT LOCK ASSEMBLY

(71) Applicant: SHL MEDICAL AG, Zug (CH)

(72) Inventor: Anders Holmqvist, Värmdo (SE)

(73) Assignee: SHL MEDICAL AG, Zug (CH)

( * ) Notice: Subject to any disclaimer, the term of this patent is extended or adjusted under 35 U.S.C. 154(b) by 148 days.

(21) Appl. No.: 17/545,235

(22) Filed: Dec. 8, 2021

(65) Prior Publication Data

US 2022/0096733 A1 Mar. 31, 2022

Related U.S. Application Data

(63) Continuation of application No. 16/612,246, filed as application No. PCT/EP2018/061880 on May 8, 2018, now Pat. No. 11,224,688.

(30) Foreign Application Priority Data

May 9, 2017 (EP) .................................... 17170306

(51) Int. Cl.
*A61M 5/00* (2006.01)
*A61M 5/20* (2006.01)
*A61M 5/24* (2006.01)

(52) U.S. Cl.
CPC .......... *A61M 5/002* (2013.01); *A61M 5/2033* (2013.01); *A61M 5/24* (2013.01); *A61M 2005/2073* (2013.01)

(58) Field of Classification Search
CPC ...... A61M 5/002; A61M 5/2033; A61M 5/24; A61M 2005/2073
USPC ....................................................... 604/135
See application file for complete search history.

(56) References Cited

U.S. PATENT DOCUMENTS

| | | | | |
|---|---|---|---|---|
| 2010/0298780 A1* | 11/2010 | Laiosa | ................ | A61M 5/2033 604/198 |
| 2013/0289491 A1 | 10/2013 | Kramer et al. | | |
| 2014/0303556 A1* | 10/2014 | Travanty | ................ | A61P 15/08 604/111 |

FOREIGN PATENT DOCUMENTS

| | | |
|---|---|---|
| CH | 710923 A2 | 9/2016 |
| CN | 1913932 A | 2/2007 |
| CN | 103764206 A | 4/2014 |
| CN | 103945881 A | 7/2014 |
| CN | 103957964 A | 7/2014 |
| CN | 104321102 A | 1/2015 |

(Continued)

*Primary Examiner* — Theodore J Stigell
*Assistant Examiner* — Nidah Hussain
(74) *Attorney, Agent, or Firm* — MCDONNELL BOEHNEN HULBERT & BERGHOFF LLP (57) ABSTRACT

A transport lock assembly for a medicament delivery device, wherein the transport lock assembly comprises a powerpack (30) having a locking member (50, 50', 50") configured to interact with a control member (60), which locking member (50, 50', 50") is movable, relative to the control member (60), from a first state in which the control member (60) is immobilized, to a second state in which the control member (60) is free to move; wherein the transport lock assembly further comprises a housing part (20) having a key member (22), such that assembly of the powerpack (30) with the housing part (20) causes the key member (22) to move the locking member (50, 50', 50") from the first state to the second state.

16 Claims, 8 Drawing Sheets

(56) References Cited

FOREIGN PATENT DOCUMENTS

| | | | |
|---|---|---|---|
| CN | 104780962 | A | 7/2015 |
| CN | 105188806 | A | 12/2015 |
| CN | 206063506 | U | 4/2017 |
| GB | 2477487 | A | 8/2011 |
| JP | 2013509215 | A | 3/2013 |
| TW | I428160 | B | 3/2014 |
| WO | 2012073032 | A1 | 6/2012 |
| WO | 2014154491 | A1 | 10/2014 |
| WO | 2016/055438 | A1 | 4/2016 |
| WO | 2016169748 | A1 | 10/2016 |

\* cited by examiner

TRANSPORT LOCK ASSEMBLY, AND A MEDICAMENT DELIVERY DEVICE COMPRISING THE TRANSPORT LOCK ASSEMBLY

CROSS REFERENCE TO RELATED APPLICATIONS

The present application is a continuation of U.S. patent application Ser. No. 16/612,246, filed Nov. 9, 2019, which is a U.S. National Phase Application pursuant to 35 U.S.C. § 371 of International Application No. PCT/EP2018/061880 filed May 8, 2018, which claims priority to European Patent Application No. 17170306.9 filed May 9, 2017. The entire disclosure contents of these applications are hereby incorporated by reference into the present application.

TECHNICAL FIELD

The present disclosure relates to a transport lock assembly for a medicament delivery device. More in particular, it relates to transport lock of a powerpack of a medicament delivery device.

BACKGROUND

The disclosure relates to medicament delivery devices that are delivered as sub-assemblies for final assembly into, for instance, auto-injectors. One of the sub-assemblies may be a powerpack, which may comprise a pre-tensioned plunger rod, arranged with a control member that is configured to release the pre-tensioned plunger rod in the assembled medicament delivery device. For this reason, the control member is movable, so that another element, typically comprised in a different sub-assembly, may interact with control member when the user of the medicament delivery device intends to administer a dose of medicament. During transport of the sub-assemblies, vibrations, movements and impacts may lead to accidental release of the pre-tensioned plunger rods, causing the powerpacks in question to be wasted. It is therefore necessary to ensure that the control members are held securely so that they do not accidentally activate the powerpacks. At the same time, the locked powerpacks must not become difficult or complicated to unlock and/or to assemble due to these security measures.

Some attempts have been made to solve these problems. WO2014/154491 discloses a transport lock mechanism for a powerpack where an actuator sleeve is prevented from axial movement during transportation. During assembly, a key member, arranged on an inner surface of a housing, interacts with the lock mechanism to rotate the actuator sleeve into a position in which it may move axially after assembly. In the present disclosure, the control member is rotationally locked. Therefore a different mechanism is needed.

WO2016/169748, on the other hand, relates to a transport lock where a powerpack comprises a rotatable coupling member which controls the release of a biased plunger rod. During transportation, the coupling member is prevented from rotation by radially flexible tabs, such that when the power pack is assembled with a housing, the tabs are pushed radially inwards to free the coupling member for rotation in the assembled medicament delivery device. Due to tolerances, the unlocking of the coupling member during assembly is not always successful, which may leady to malfunctioning medicament delivery devices.

SUMMARY

In the present disclosure, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

Further, the term "longitudinal", with or without "axis", refers to a direction or an axis through the device or components thereof in the direction of the longest extension of the device or the component.

The term "lateral", with or without "axis", refers to a direction or an axis through the device or components thereof in the direction of the broadest extension of the device or the component. "Lateral" may also refer to a position to the side of a "longitudinally" elongated body.

In a similar manner, the terms "radial" or "transversal", with or without "axis", refers to a direction or an axis through the device or components thereof in a direction generally perpendicular to the longitudinal direction, e.g. "radially outward" would refer to a direction pointing away from the longitudinal axis.

Also, if nothing else is stated, in the following description wherein the mechanical structure of the device and the mechanical interconnection of its components is described, the device is in an initial non-activated or non-operated state.

In view of the foregoing, a general object of the present disclosure is to provide a transport lock assembly for a powerpack of a medicament delivery device.

According to a main aspect of the disclosure it is characterised by a transport lock assembly for a powerpack of a medicament delivery device, wherein the transport lock assembly comprises a powerpack having a spring-biased drive member, a body for holding the spring-biased drive member in a pre-tensioned state, a control member for releasing the spring-biased drive member from the body, and a locking member configured to interact with the control member, which locking member is movable, relative to the control member, from a first state in which the control member is immobilized, to a second state in which the control member is free to move, the transport lock assembly being further characterised by a housing part having a key member, which housing part is configured to receive the powerpack, and wherein assembly of the powerpack with the housing part causes the key member to move the locking member from the first state to the second state relative to the control member.

The locking member thus connects with the control member and prevents the control member from rotating when the locking member is in the first state. The locking member is further disconnected from the control member when the power pack is assembled with the housing part, such that the locking member is moved to the second state, wherein the control member is free to rotate.

The body comprises radially flexible arms. The arms connect with an engagement member of the spring-biased plunger rod. In an initial state of the control member, the control member prevents the arms from flexing radially outwards, out of engagement with the engagement member of the plunger rod. In a released state of the control member, relative to the body, recesses on an inside surface of the control member align with the arms of the body. The recesses of the control member allow the arms to flex radially outwards, under a bias of a drive member spring, releasing the spring-biased drive member to expel a medicament of a container.

According to another aspect of the disclosure the control member is rotationally movable around a longitudinal axis, but axially fixed, relative to the body, and the locking member is axially movable relative to the body and relative to the control member.

Since the control member is axially fixed, the locking member will disengage from the control member upon axial movement from the first state to the second state.

According to another aspect of the disclosure, assembly of the powerpack with the housing part comprises an axial movement of the powerpack relative to the housing part such that the key member axially moves the locking member from the first state to the second state.

Thus, the key member may be a structural feature of the housing part, which structural feature interacts with a surface, directly connected to the locking member, to axially move the locking member from the first state to the second state. The key member may also a structural feature of component contained in the housing part on assembly of the powerpack with the housing part.

According to another aspect of the disclosure, the locking member, in the first state, mates with a mating member of the control member such that rotation of the control member relative to the body and relative to the locking member is prevented. The locking member, in the second state, is axially separated from the mating member of the control member such that rotation of the control member relative to the body and relative to the locking member is allowed.

The mating member of the control member and the locking member may be any kind of mutually engaging structures, such as protrusions, ratchets, ribs, recesses, teeth, slits, etc, which prevent relative rotation between the control member and the locking member in the first state, but which allow relative rotation between the control member and the locking member in the second state, and which also allow axial separation, or disengagement, of the mating member and the locking member.

According to another aspect of the disclosure the body is coaxially arranged with the control member and the spring-biased drive member.

The body may be a tubular sleeve, accommodating the spring-biased drive member.

According to another aspect of the disclosure the body is located radially outside the spring-biased drive member and radially inside the control member, and the locking member is located axially next to the control member.

As such, the control member may be a tubular sleeve which is rotationally arranged radially outside the body. The locking member may also be tubular, or ring-shaped, and may be axially movable relative to, and next to, the control member.

According to another aspect of the disclosure the locking member is arranged on a support member which is rotationally fixed relative to the body.

Since the locking member is arranged on the support member, which is rotationally fixed relative to the body, the control member is also rotationally fixed relative to the body, when the locking member is in the first state. In other words, the locking member prevents the control member from rotational movement when the locking member is in the first state.

According to another aspect of the disclosure the support member is axially movable relative to the body and relative to the control member.

The locking member is arranged on the support member. Therefore, the locking member is movable from the first state to the second state as the support member moves axially relative to the control member.

According to another aspect of the disclosure the support member is axially flexible.

The support member may be an axially flexible member, wherein axial compression or extension of the flexible support member causes the locking member to move from the first state to the second state.

According to another aspect of the disclosure the support member is an axially flexible sleeve coaxially arranged with the body.

The support member may be an axially flexible sleeve, or tubular member, wherein axial compression or extension of the flexible support member causes the locking member to move from the first state to the second state.

According to another aspect of the disclosure the support member is an axially flexible, integrated, unitary part of the body.

To reduce the number of molded components of the device, the support member and the locking member may be integral with the body.

A flexible and/or resilient support member be advantageous in that it provides an inherent resilient force which may return the locking member into engagement with the mating member of the control member in case the members have been accidentally disengaged during handling or transport of the powerpack.

According to another aspect of the disclosure, a medicament delivery device comprises a transport lock assembly according to any of the foregoing aspects of the disclosure.

DETAILED DESCRIPTION

Figure 1:
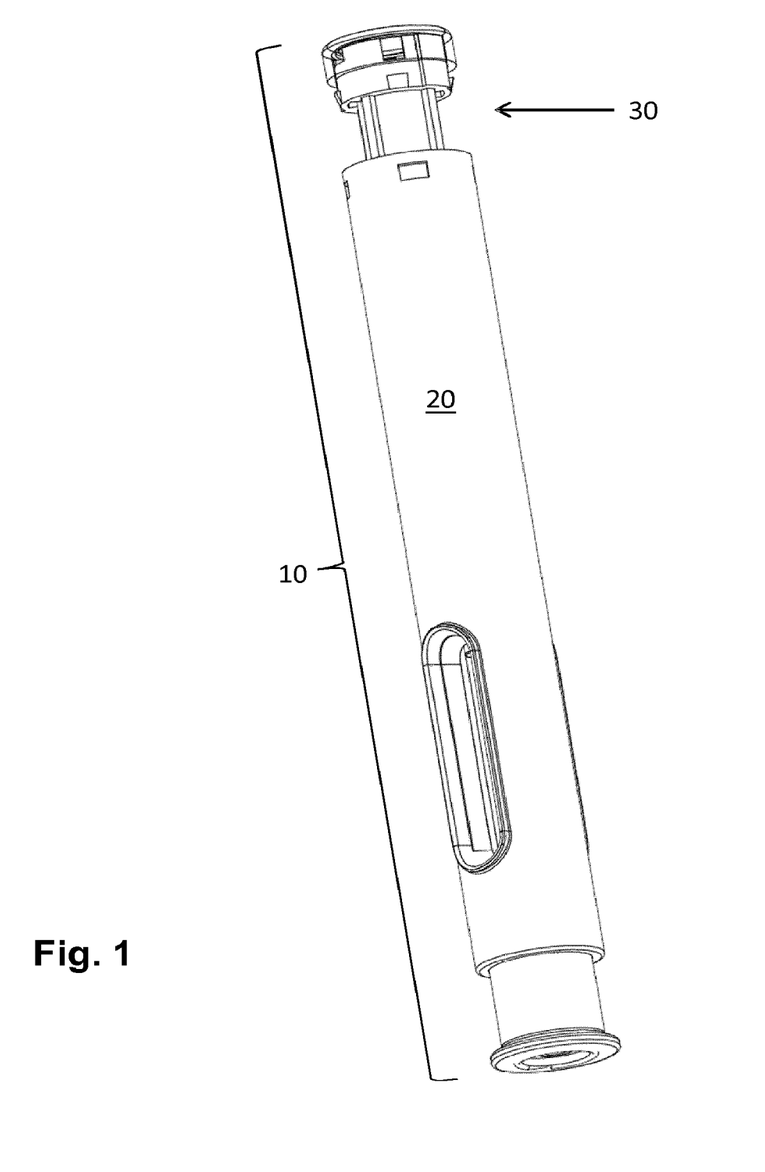
FIG. 1 a perspective view of a semi-assembled medicament delivery device according to the present disclosure FIG. 2 a cross-sectional view of the semi-assembled medicament delivery device of FIG. 1
Figure 2:
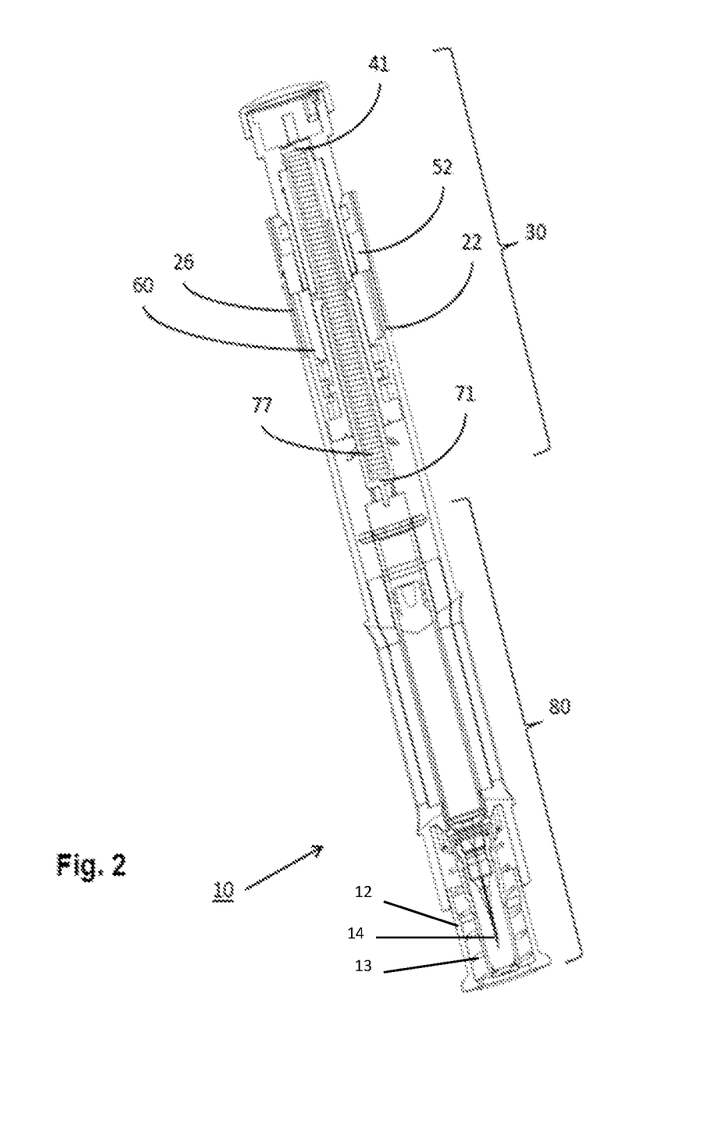

FIGS. 1 and 2 show a medicament delivery device 10 in a semi-assembled state in which a front assembly 80 has been mounted in a proximal part of a housing part 20 and in which a powerpack 30 has been partly inserted via a distal end of the housing part 20.

The front assembly 80 comprises a pre-filled medicament container, having a movable stopper sealing a distal end of the container. A container holder may be provided to retain the medicament container within the housing part 20. A proximal end of the container may comprise a fixedly attached medicament delivery member, such as an injection needle or a mouthpiece. The medicament delivery member may alternatively be designed to be attached to the container, via the container holder at a later stage, before use of the medicament delivery device. In case the medicament delivery member is a fixedly attached injection needle, a needle sheath is provided to protect the injection needle in a sterile environment until the medicament delivery device 10 is ready for use.

A spring-biased tubular medicament delivery member guard 12 is operatively engaged with spring 13 and is movably arranged at a proximal end of the housing part 10. The medicament delivery member guard serves to protect and conceal the medicament delivery member 14, and to activate the powerpack 30 of an assembled medicament delivery device.

The proximal end of the housing part 20 may further be provided with a removable cap (not shown). In case the container has a fixedly attached injection needle with a needle sheath, the cap may also be provided with a needle sheath remover (not shown), such that the needle sheath is removed from the needle when the cap is removed from the proximal end of the housing part 20.

Figure 3:
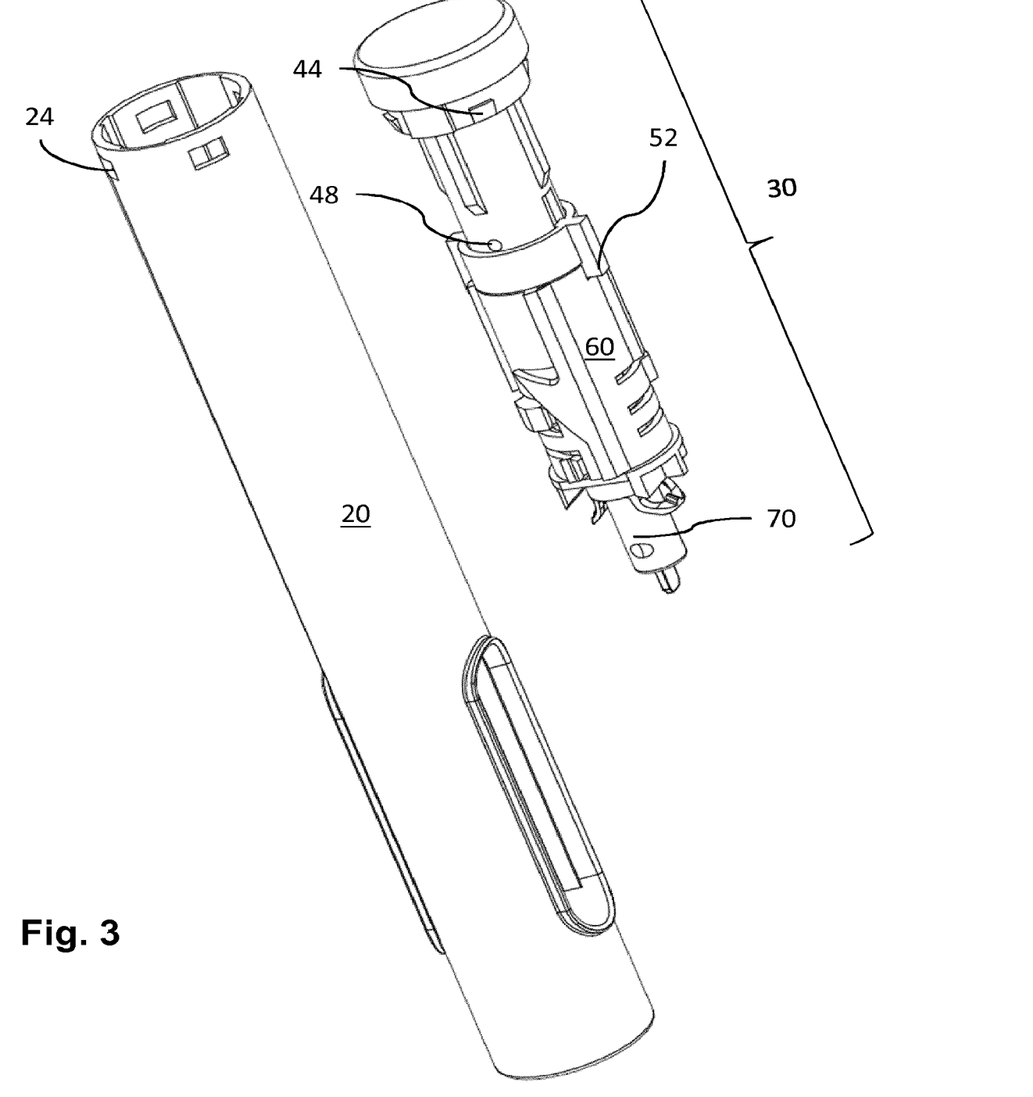
FIG. 3 a perspective view of a housing part and of a powerpack of the present disclosure FIG. 4 an exploded view of the powerpack of FIG. 3

FIG. 3 shows a main aspect of the present disclosure, namely the housing part 20 and the powerpack 30 in an unassembled state. The constituent mechanical parts of the medicament delivery device 10 are transported and delivered as sub-assemblies to a site where final assembly is carried out. Final assembly means the process of assembling the sub-assemblies together with the pre-filled medicament container.

Figure 4:
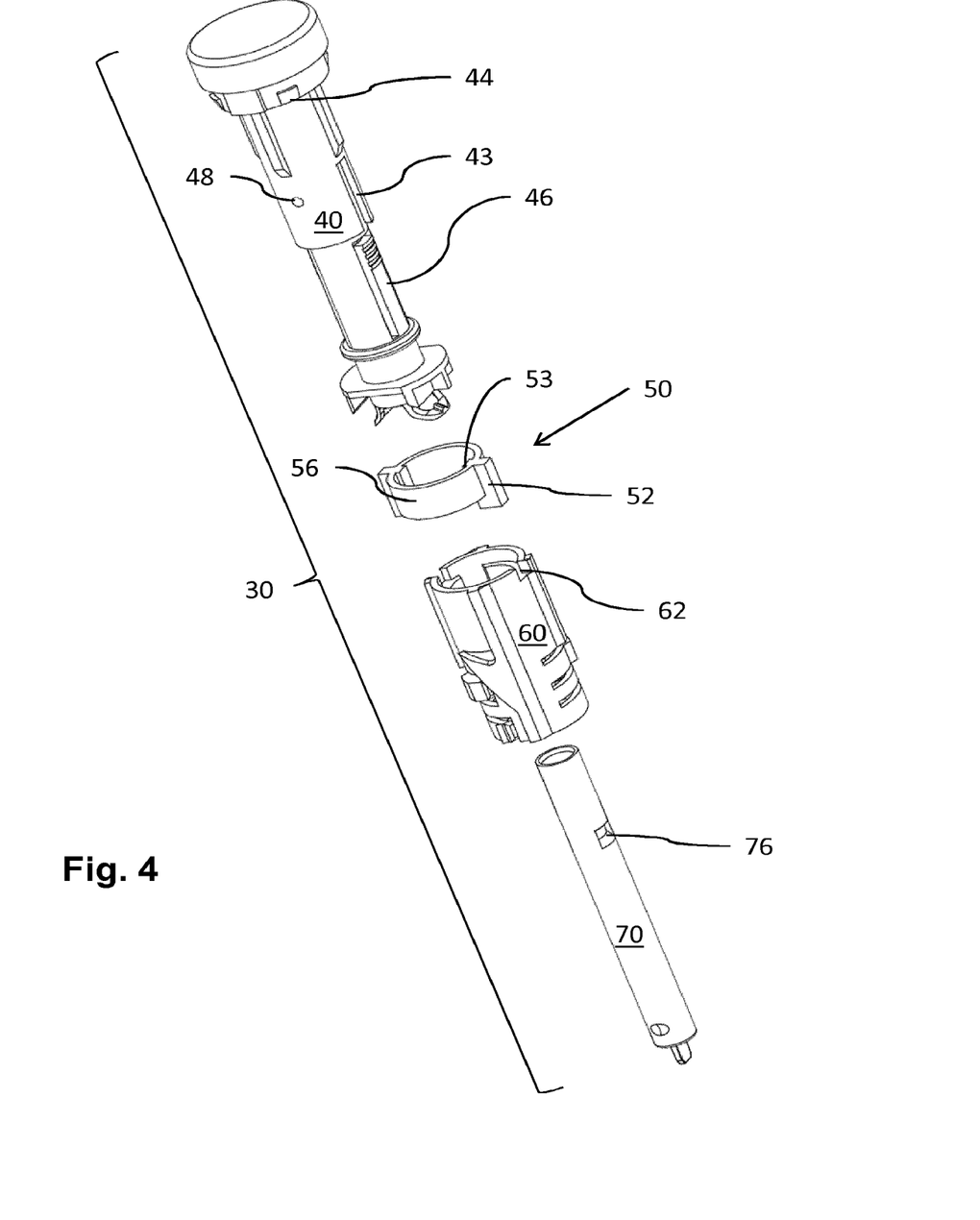

As shown in FIG. 4, the powerpack 30 comprises a spring-biased drive member 70 (spring shown in FIG. 2), e.g. a plunger rod, a body 40 for holding the spring-biased drive member 70 in a pre-tensioned state, a movable control member 60 for releasing the spring-biased drive member 70, and a locking member 50, configured to interact with the control member, which locking member 50 is movable, relative to the control member 60, from a first state in which the control member 60 is immobilized, to a second state in which the control member 60 is free to move.

The spring-biased drive member 70, further comprises a spring 77 (FIG. 2), which is pre-tensioned between a proximal inner surface 71 of the drive member 70, and distal inner stop wall 41 of the body 40.

The body 40 may be generally tubular, and may comprise a radially flexible holding member 46, such as an arm having an inward protrusion, which engages a corresponding holding member 76, e.g. a recess, of the spring-biased drive member 70, in order to hold the spring-biased drive member 70 in the pre-tensioned state. The drive member 70 is coaxial with the body 40 and is located radially inside the body 40. The control member 60 may be tubular and is coaxial with the body 40, and is further located radially outside the body 40. An inner surface of the control member 60 abuts the holding member 46 such that it is prevented from flexing radially outwards under the bias of the spring 77 when the control member 60 is in an initial state.

If the control member 60 is moved to a released state, such as by interaction with the medicament delivery member guard, or by accident, recesses on the inside surface of the control member 60 align with the holding member 46 such that the holding member 46 may flex radially outwards into the recesses, due to the spring 77 forcing the spring-biased drive member forward. Thereby the holding member 46 is forced outwards out of the corresponding holding member 76. When the holding member 46 is disengaged from the corresponding holding member 76, the spring-biased drive member 70 will move proximally. If the medicament delivery device is completely assembled, the spring-biased drive member 70 will abut the stopper of the medicament container, and will consequently drive the stopper forward, proximally, and expel a medicament through the medicament delivery member.

If the control member 60 is somehow, e.g. by accident, moved to the released state before the medicament delivery device 10 is completely assembled, the spring-biased drive member 70 will be catapulted out of the powerpack 30, which may be harmful to a person handling the device. In addition, the powerpack 30 will be wasted.

In order to mitigate the problem of accidental activation of the powerpack 30, the control member 60 must be prevented from moving to the released state prematurely.

In the exemplified embodiment, a locking member 50 is provided to prevent the control member 60 from moving relative to the body 40. More in particular, the control member 60 is rotationally movable around a longitudinal axis, and axially fixed, relative to the body 40, and the locking member 50 is axially movable, and rotationally locked relative to the body 40 and relative to the control member 60. However, the locking member 50 is configured to interact with the control member 60, such that when the locking member 50 is in the first state, the control member 60 is immobilized by the locking member 50. When the locking member 50 is moved to the second state the control member 60 is released by the locking member 50.

The locking member 50 may move either by axial displacement, e.g. along the body 40, or by axial compression, such that at least a part of the locking member is compressed, causing the locking member 50 to disengage from the control member 60. The locking member 50 may alternatively move by a combination of displacement and compression. The locking member 50 may be located axially next to the control member 60.

The locking member 50 may comprise support member 56, which may be an annular or tubular member arranged around the body 40. The locking member 50 may further comprise and a mating member 52, arranged on the support member 56. The mating member 52 may be configured as a longitudinally elongated protrusion, which in the first state mates with a corresponding mating member 62 of the control member 60, such as a longitudinally elongated recess of the control member 60, such that rotation of the control member 60 relative to the body 40 and relative to the locking member 50 is prevented. In the second state, the mating member 52 of the locking member 50, is axially separated from the corresponding mating member 62 of the control member 60 such that rotation of the control member 60 relative to the body and relative to the locking member is allowed.

As shown in FIG. 4, the locking member 50 may comprise a fixing element 53 which may interact with a corresponding fixing element 43 of the body 40 such that the locking member 50 is axially movable but rotationally fixed relative to the body 40. The fixing element 53 may be an inwardly directed protrusion such as a rib, and the corresponding fixing element 43 may be a longitudinally directed depression such as a groove or a slot in a side wall of the body 40. As is common in the art, interacting protrusions and depressions may be interchanged between the components, such that the protrusion is instead arranged on the body 40 and the depression is arranged on an inner wall of the locking member 50.

As described above, the movement of the locking member 50 may be an axial displacement in relation to the body 40 and to the control member 60, or an axial compression of the locking member 50, or a combination of compression and displacement. As such, the displacement is a movement of the support member 56 and the mating member 52 arranged thereon. The compression movement is an axial compression of the support member 56 such that the mating member 52 arranged thereon is axially displaced in relation to the body 40 and to the control member 60.

The housing part 20 is configured to receive the powerpack 30. The housing part 20 comprises a key member 22 configured to interact with the locking member 50, such that on assembly of the housing part 20 with the power pack 30, the key member 22 axially moves the locking member 50 from the first state to the second state. Thereafter, the control member 60 is free to move to release the spring-biased drive member 70 upon activation of the medicament delivery device 10.

The key member 22 may be configured as a distally directed ledge 22, provided at a proximal end of a longitudinal guide 26. The mating member 52 of the locking member 50 may be configured as a guide follower such that the mating member 52 slides along the guide 26 when inserting the powerpack 30 in the housing part 20. Alternatively, the key member 22 may be configured as a structural feature, e.g. a ledge, or a protrusion, of any of the components comprised in the front assembly 80 in the housing part 20.

In a first embodiment, shown in FIGS. 1-5b, the support member 56 of the locking member 50 is configured as a generally rigid annular or tubular member, arranged around the body 40. A stop element 48, such as a bump or a slight protrusion, is provided on an outer surface of the body 40. The stop element 48 abuts the locking member 50 in the first state, such that a certain threshold force is required to move the locking member 50 from the first state to the second state, in order to prevent unintentional movement of the locking member 50.

Upon insertion of the powerpack 30 in the housing part 20, the mating member 52 of the locking member 50 slides along the guide 26 of the housing part 20. At a certain pre-determined position, the mating member 52 makes contact with the key member 22. On application of said certain threshold force the powerpack 30 may be further inserted into the housing part 20, causing the key member 22 to axially move the locking member 50 from the first state (FIGS. 2 and 3) to the second state (FIGS. 5a and 5b), during which movement the locking member 50 rides over the stop element 48. The locking member 50 is thereby displaced axially away from the control member 60, such that the control member 60 is free to move.

Figure 5A:
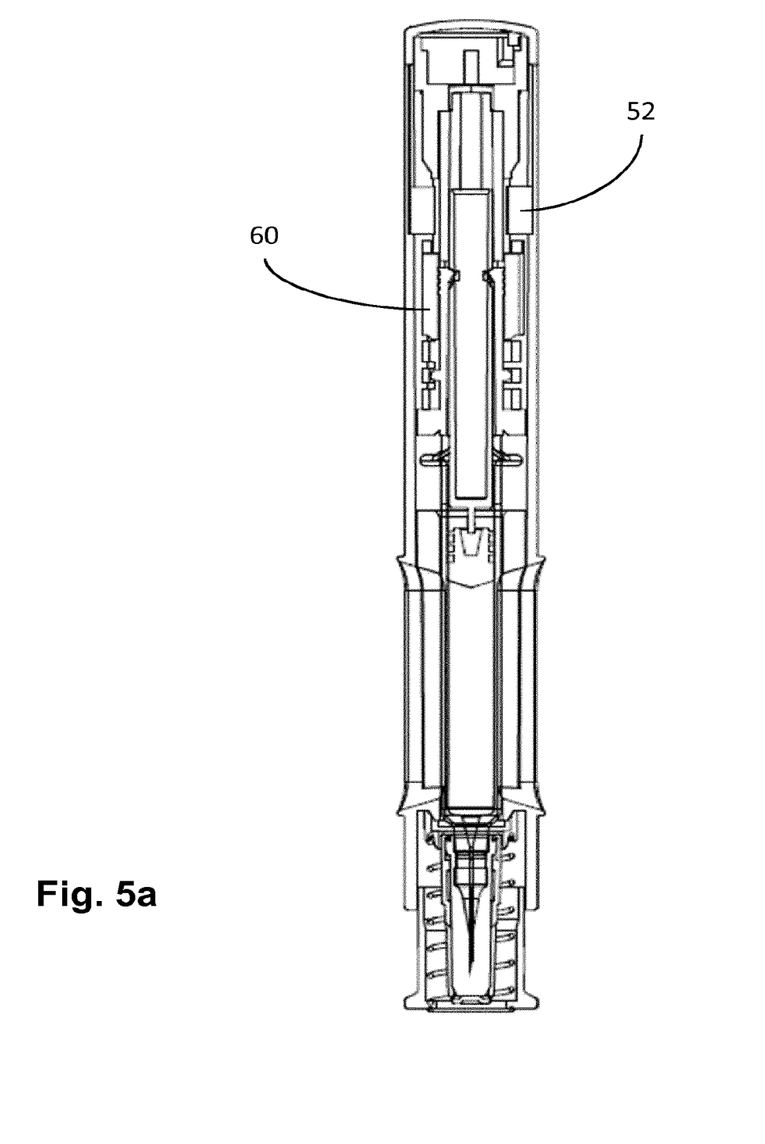
FIG. 5*a-b* cross-sectional views of an assembled medicament delivery device according to the present disclosure FIG. 6*a-b* perspective views of a powerpack according to a further embodiment of the present disclosure FIG. 7*a-b* perspective views of a powerpack according to another embodiment of the present disclosure
Figure 5B:
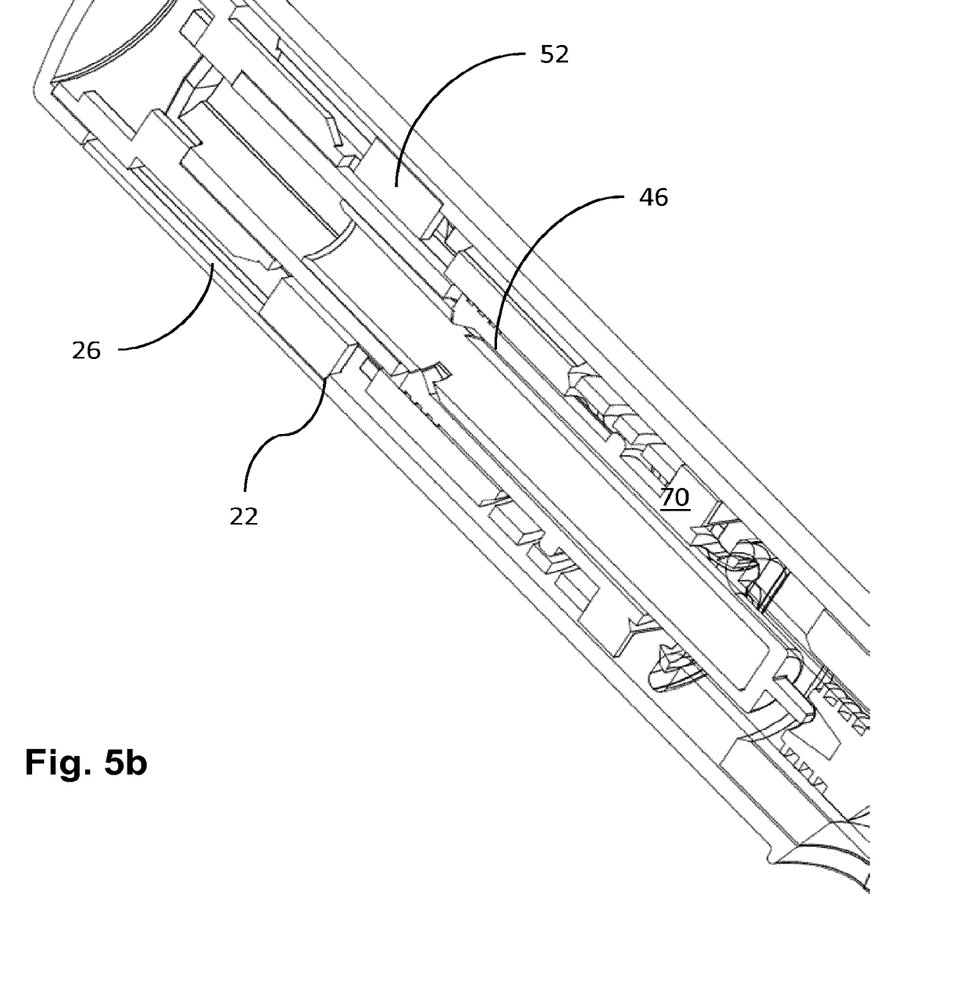

Towards the end of the insertion, fastening elements 44 of the body 40 engage with corresponding fastening elements 24 of the housing part 20, e.g. by snap-fit engagement, such that the body 40, and consequently the powerpack 30, and the housing part 20 are locked to each other.

Figure 6A:
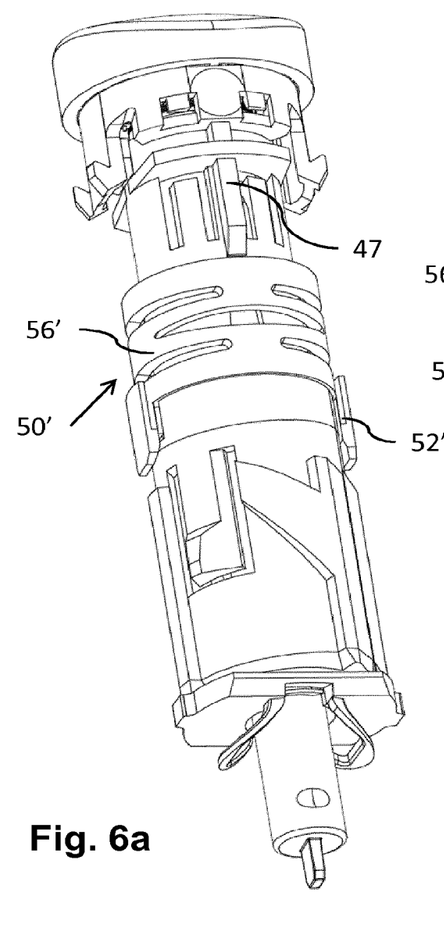
Figure 6B:
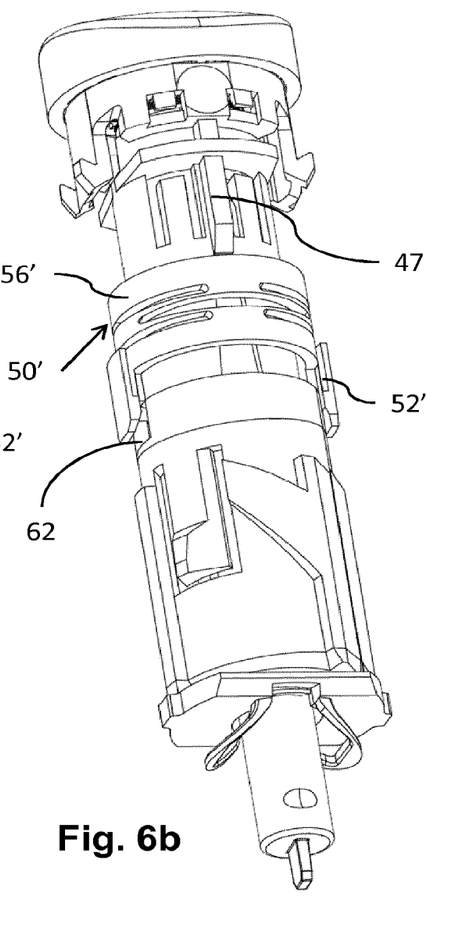

In a second embodiment, shown in FIGS. 6a and 6b, a support member 56' of the locking member 50' is configured as an axially resiliently compressible annular, tubular, or sleeve-like member, arranged around the body 40. A distal end of the support member 56' rests against a blocking member 47 such that the support member 56' is prevented from distal displacement. A mating member 52' of the compressible support member 56' is engaged with the corresponding mating member 62 of the control member 60 (FIG. 6a). A certain threshold force is required to compress the support member 56' axially in order to disengage the mating member 52' from the corresponding mating member 62 (FIG. 6b).

Upon insertion of the powerpack 30 in the housing part 20, the mating member 52' of the locking member 50' slides along the guide 26 of the housing part 20. At a certain pre-determined position, the mating member 52' makes contact with the key member 22. On application of said certain threshold force the powerpack 30 may be further inserted into the housing part 20, causing the key member 22 to axially move, e.g. compress, the locking member 50' from the first state (FIG. 6a) to the second state (FIG. 6b), during which movement the mating member 52' is disengaged from the corresponding mating member 62.

The resilience of the support member 56' constantly biases the mating member 52' into engagement with the corresponding mating member 62. Therefore, if the mating member 50' should be accidentally moved, i.e. compressed, during handling or transport of the powerpack 30, such as by an impact, the mating member 52' will instantly re-engage with the corresponding mating member 62 due to the resilience of the support member 56'.

Figure 7A:
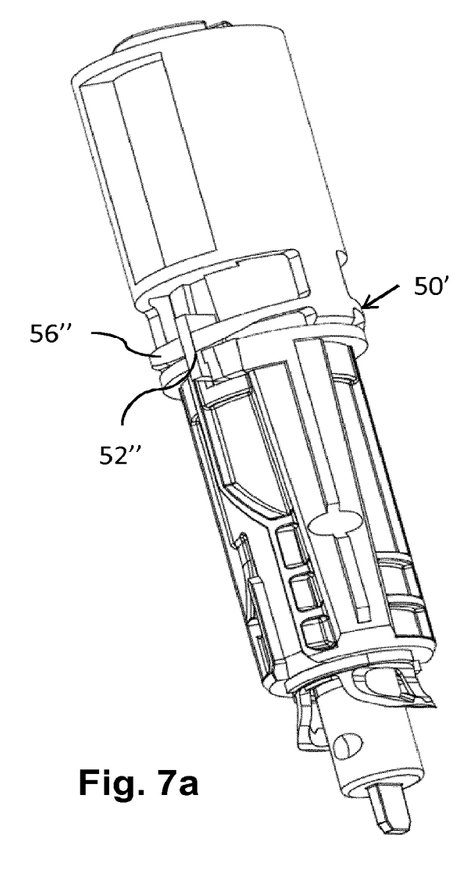
Figure 7B:
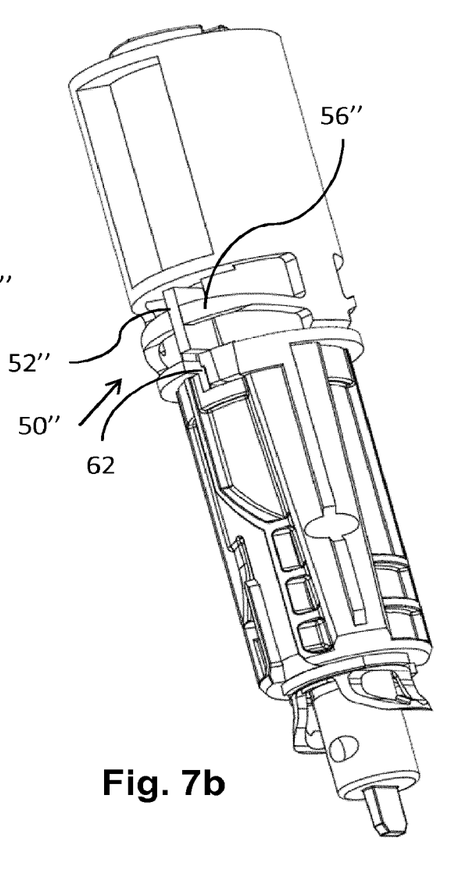

In a third embodiment, shown in FIGS. 7a and 7b, a support member 56" of the locking member 50" is configured as an axially resiliently compressible member which is an integrated unitary part of the body 40. A distal end of the support member 56" is integrated with the body 40 such that the support member 56" is prevented from distal displacement. A mating member 52" of the compressible support member 56" is engaged with the corresponding mating member 62 of the control member 60 (FIG. 7a). A certain threshold force is required to compress the support member 56" axially in order to disengage the mating member 52" from the corresponding mating member 62 (FIG. 7b).

Upon insertion of the powerpack 30 in the housing part 20, the mating member 52" of the locking member 50" slides along the guide 26 of the housing part 20. At a certain pre-determined position, the mating member 52" makes contact with the key member 22. On application of said certain threshold force the powerpack 30 may be further inserted into the housing part 20, causing the key member 22 to axially move, e.g. compress, the locking member 50" from the first state (FIG. 7a) to the second state (FIG. 7b), during which movement the mating member 52" is disengaged from the corresponding mating member 62. The locking member 50" is thereby moved axially away from the control member 60, such that the control member 60 is free to move.

An integrated locking member 50" means fewer components to assemble and reduces the tolerance chain, which leads to a more robust and reliable device. Furthermore, as discussed above in conjunction with the second embodiment, the resilience of the locking member 50" will cause the mating member 52" to re-engage with the corresponding mating member 62 if the locking member 50" should be accidentally moved during handling or transport of the powerpack 30.

The invention claimed is:

1. A medicament delivery device comprising:
a housing having an open terminal distal end and an inner surface comprising a key member;
a body comprising a tubular portion and an end cap portion, where the body is configured so that it can slide axially relative to the distal end of the housing from a first axial position to a second axial position;
a drive member movable relative to the housing;
a control member rotatably positioned on the tubular portion of the body and having a first mating member;
a locking member slidably positioned on the body and having a second mating member configured to engage with the first mating member, wherein when the body is in the first axial position, the first and second mating members
are engaged such that the control member is rotatably fixed relative to the tubular portion,
wherein the body is located radially outside the drive member and radially inside the control member,
wherein movement of the body from the first position to the second position causes the key member to engage with the locking member such that the locking member moves distally relative to the control member causing the second mating member to disengage from the first mating member, and
wherein when the body is in the second axial position the first and second mating members are not engaged such that the control member can rotate relative to the housing and the tubular portion.

2. The medicament delivery device of claim 1, wherein the housing further comprises a first fastener and the body further comprises a second fastener configured to engage the first fastener.

3. The medicament delivery device of claim 2, wherein movement of the body from the first position to the second position causes the first and second fasteners to engage and lock the cap portion to the housing such that the body is axially and rotationally fixed relative to the housing.

4. The medicament delivery device of claim 1, wherein the drive member is hollow.

5. The medicament delivery device of claim 4 further comprises a pretensioned spring positioned within the drive member to bias the drive member in a proximal direction.

6. The medicament delivery device of claim 5, wherein the tubular portion further comprises a flexible holding member engaged with the drive member to prevent proximal axial movement of the drive member.

7. The medicament delivery device of claim 4, wherein the body is coaxially arranged with the control member and the drive member.

8. A medicament delivery device comprising:
a housing having an open terminal distal end and an inner surface comprising a first fastener;
a drive member movable relative to the housing;
a medicament delivery member guard partially positioned within the housing;
a body comprising a tubular portion, an end cap portion, and a second fastener configured to engage the first fastener, where the body is configured so that it can slide axially relative to the medicament delivery member guard and the distal end of the housing from a first axial position to a second axial position;
a control member rotatably positioned on the tubular portion of the body and having a first mating member;
a locking member slidably positioned on the body and having a second mating member configured to engage with the first mating member,
wherein when the body is in the first axial position, the first and second mating members
are engaged such that the control member is rotatably fixed relative to the tubular portion,
wherein the body is located radially outside the drive member and radially inside the control member,
wherein movement of the body from the first position to the second position causes the
locking member to move distally relative to the control member and causes the second mating member to disengage from the first mating member, and
wherein when the body is in the second axial position:
the first and second fasteners are engaged such that the body is axially fixed relative to the housing; and
the first and second mating members are not engaged such that the control member can rotate relative to the housing and the tubular portion.

9. The medicament delivery device of claim 8, wherein the housing further comprises a first fastener and the body further comprises a second fastener configured to engage the first fastener.

10. The medicament delivery device of claim 8, wherein movement of the body from the first position to the second position causes the first and second fasteners to engage and lock the cap portion to the housing such that the body is axially and rotationally fixed relative to the housing.

11. The medicament delivery device of claim 8, wherein the medicament delivery member guard biased in a proximal direction.

12. The medicament delivery device of claim 8, wherein movement of the body from the first position to the second position causes the first and second fasteners to engage and lock the cap portion to the housing such that the body is axially and rotationally fixed relative to the housing.

13. The medicament delivery device of claim 8, wherein the drive member is hollow.

14. The medicament delivery device of claim 12 further comprises a pretensioned spring positioned within the drive member to bias the drive member in a proximal direction.

15. The medicament delivery device of claim 13, wherein the tubular portion further comprises a flexible holding member engaged with the drive member to prevent proximal axial movement of the drive member.

16. The medicament delivery device of claim 12, wherein the body is coaxially arranged with the control member and the drive member.

\* \* \* \* \*